United States Patent [19]
Buckson

[11] 3,970,857
[45] July 20, 1976

[54] APPARATUS FOR WEB DEFECT DETECTION INCLUDING A WEB SWATCH THAT CONTAINS A DEFECT

[75] Inventor: Gerald Irving Buckson, Wilmington, Del.

[73] Assignee: E. I. Du Pont de Nemours and Company, Wilmington, Del.

[22] Filed: Aug. 6, 1975

[21] Appl. No.: 602,466

[52] U.S. Cl. .............................. 250/563; 250/572; 356/200
[51] Int. Cl.² ........................................ G01N 21/32
[58] Field of Search ........... 250/561, 562, 563, 571, 250/572, 214 R, 214 RC; 209/111.7; 356/199, 200, 237

[56] References Cited
UNITED STATES PATENTS

| | | | |
|---|---|---|---|
| 3,061,731 | 10/1962 | Thier et al. .......................... | 250/563 |
| 3,646,353 | 10/1970 | Bhullar et al. ....................... | 356/200 |
| 3,843,890 | 10/1974 | Anthony, Jr. et al. ............... | 250/572 |

*Primary Examiner*—Alfred E. Smith
*Assistant Examiner*—D. C. Nelms

[57] ABSTRACT

An improved web scanning inspection system that includes a fixed standard web swatch containing representative objectionable defects in the path of the scan beam at the onset of each scan in order to calibrate inspection system discriminator thresholds. Gating and logic circuits are arranged to extract amplitude and duration characteristics of the defect related portions of the signals generated by scans across the standard swatch material. These are then used to actuate an alarm whenever the inspection system discriminator circuits fail to detect the objectional defects in the standard web swatch.

2 Claims, 12 Drawing Figures

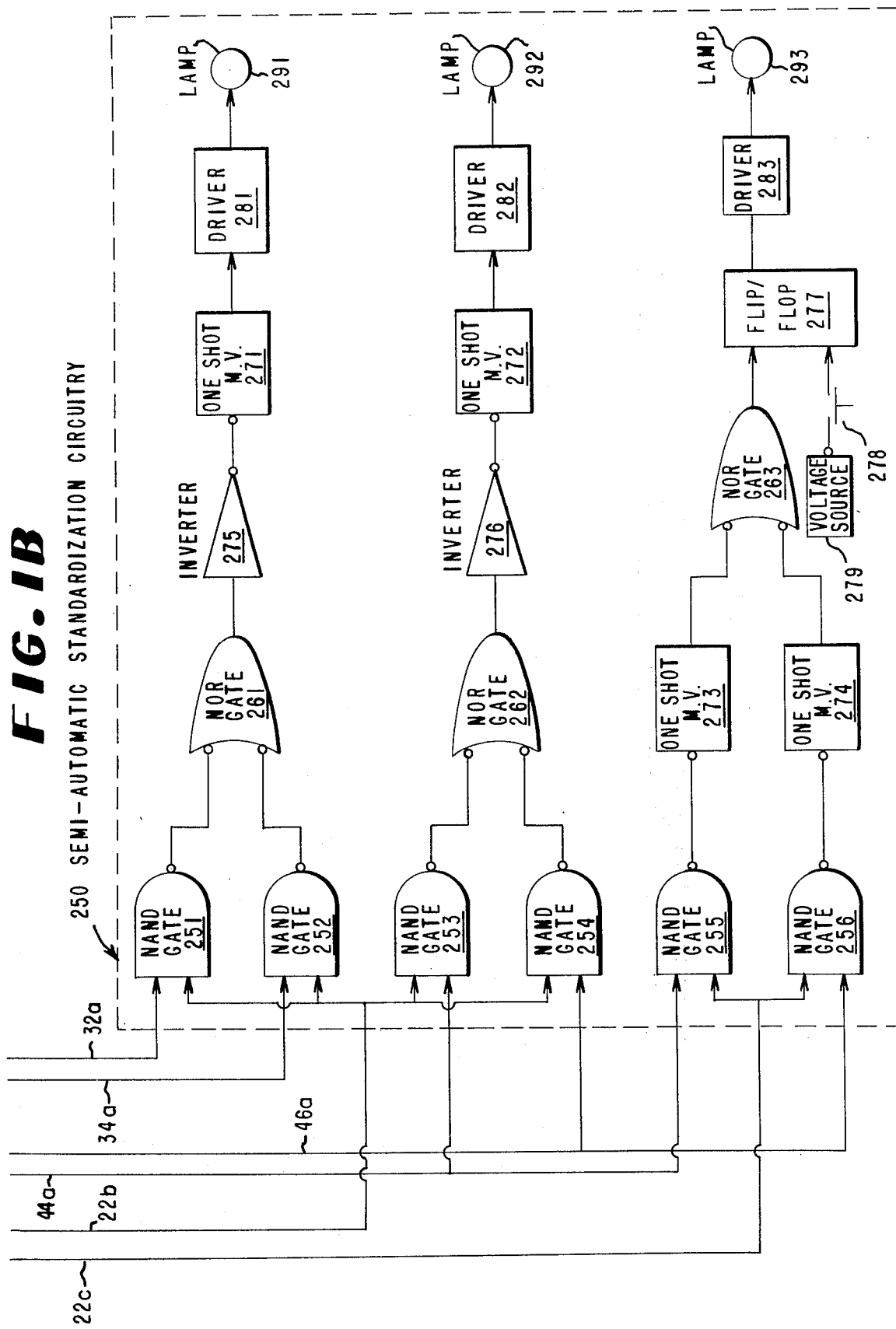

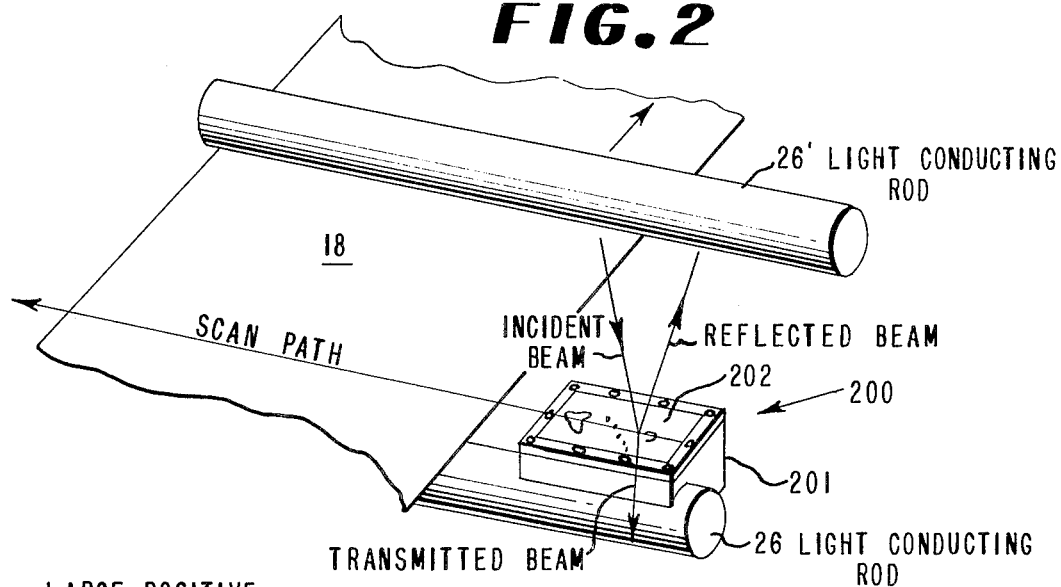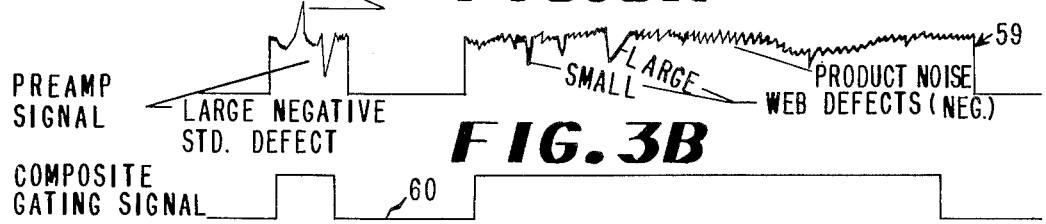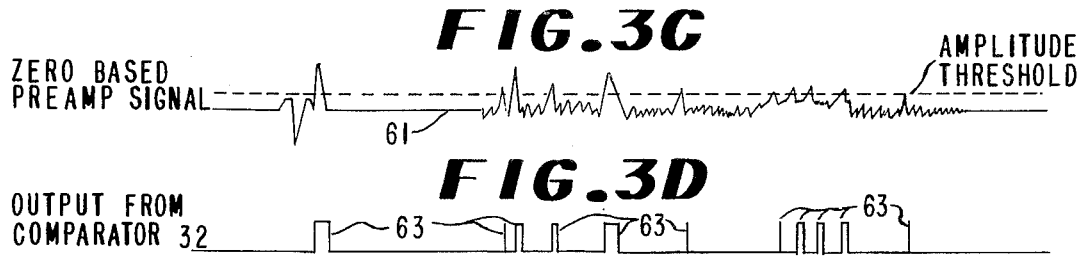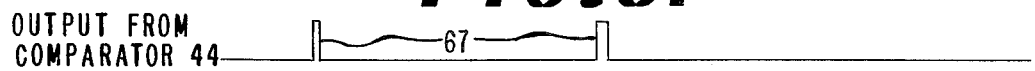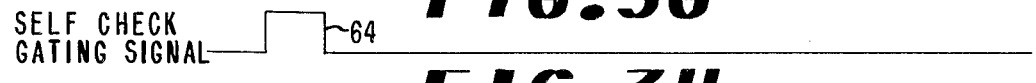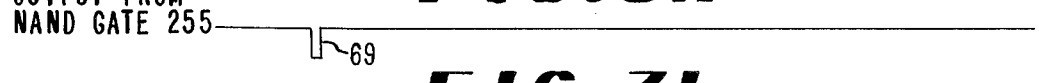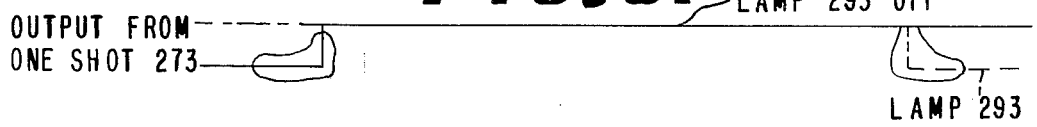

3,970,857

APPARATUS FOR WEB DEFECT DETECTION INCLUDING A WEB SWATCH THAT CONTAINS A DEFECT

BACKGROUND OF THE INVENTION

This invention relates to an electro-optical web inspection system for detecting and extracting oversize hole, clump or color related web defect signals from a noisy product scan signal. More particularly, it is concerned with auxiliary apparatus for continuously self-checking the operation of the system to determine when it fails to detect defects of predescribed character. The auxiliary equipment which comprises this invention is attached to the flying spot inspection system of U.S. Pat. No. 3,866,054 which is assigned to the assignee of this application.

The web inspection system of the above-referenced patent operates satisfactorily. However, significant expenditures of time and effort has been required in order to calibrate the discriminator circuits for proper sensitivity and to periodically check that prescribed discriminator circuit threshold levels are being maintained and proper gates are being generated.

SUMMARY OF THE INVENTION

This invention is an improved flying spot web inspection system which includes electro-optical scanning apparatus for detecting defects in a moving web and discriminator circuitry for providing alarm output logic signals when defect signal amplitudes exceed predetermined primary threshold levels in either the positive or negative direction and which maintain this excess level for a predetermined duration (i.e., a secondary threshold). The improvement comprises: (1) the addition of a standard defect swatch assembly in the path of the scanning beam and (2) associated electronic logic and gating circuitry to operate indicator lamps to alert the inspector operator to those occasions when malfunctions in the gating subsystem or either positive or negative defect discriminator circuits cause the inspection system to fail to register defects in the course of each scan across the standard defect swatch assembly. The occurrence of a lighted indicator lamp condition signifies that either (1) one or more amplitude or duration discriminator thresholds have drifted to higher absolute values, (2) there has been a decrease in scan beam intensity, or (3) proper gates are not being generated.

BRIEF DESCRIPTION OF THE DRAWINGS

FIGS. 1A and 1B are schematic drawings of the optical system with the upper light conducting rod removed for simplicity, and a circuit diagram for the overall system including the auxiliary semi-automatic standardization (SAS) attachments of this invention;

FIG. 2 is a schematic view of the standard defect swatch and holder;

FIGS. 3A through 3I are representations of key signal wave forms occurring in particular parts of the circuitry of the system.

DETAILED DESCRIPTION OF THE PREFERRED EMBODIMENT

Figure 1A:
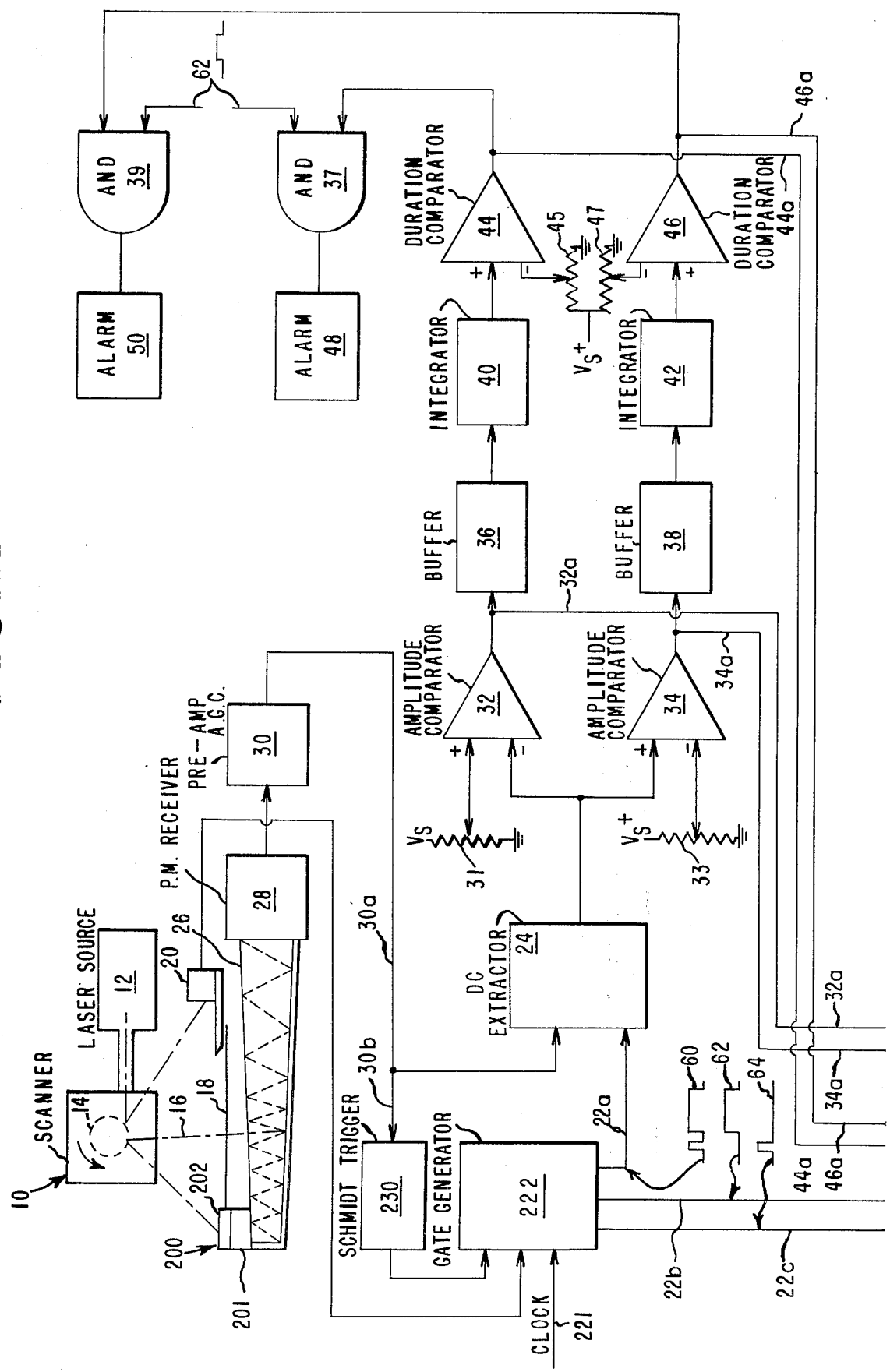

Turning first to FIGS. 1A and 1B, it is noted that this new system has many similarities to the system of FIG. 1 in U.S. Pat. No. 3,866,054 since it builds onto the latter to provide new, improved functions. Furthermore, for ease in cross reference, the same nomenclature and identifying numbers for component parts has been used wherever possible in this application as in referenced patent. Changes over the previously taught system include the relocation of photocell 20 to the opposite side of web 18 to provide a position for the addition of the standard defect swatch assembly 200 which includes a holder 201 and a swatch 202 to be described below in connection with FIG. 2. In addition, the gate generator 222 of this invention replaces the gate generator 22 of the referenced patent in order to provide three separate gating signals, namely: (1) a composite gating signal 60, (2) a product gating signal 62, and (3) a self-check gating signal 64. Further modifications include the insertion of a Schmitt trigger circuit 230 which receives its input signal 59, shown in FIG. 3A over line 30b from the preamplifier 30 at the start of each scan then provides a clipped and squared up signal as its pulse output to gate generator 222. The other input signals to gate generator 222 are received from reset photocell 20 and from a high frequency stable clock (not shown) over line 221 in order to effect time coordination for the entire inspection system. Lastly, gates 37 and 39 (FIG. 1A) are provided at the output terminals of the two discriminator circuits to limit the alarm signals 48, 50 to the product portion of the scan signal.

The composite gating signal 60, shown in FIG. 3B, travels over line 22a from gate generator 222 to DC extractor 24. This circuit functions as described in the above-referenced patent to provide a zero based signal 61, shown inverted in FIG. 3C to the input terminals of the positive and negative defect discriminators which include amplitude and duration comparator circuits 32, 34, 44 and 46 (FIG. 1A). With the exception of the four electrical lines 32a, 34a, 44a and 46a, which lead to the semi-automatic standardization (SAS) gating circuitry designated generally as element 250, the arrangement and function of the defect discriminators are as described in the afore-mentioned patent.

The product gate and self-check gate signals 62, 64, respectively, travel over line 22b and 22c, respectively, and together with the signals appearing on the four previously mentioned lines from the defect discriminator circuitry comprise the total input to the SAS circuitry 250 (FIG. 1B).

Turning now to FIG. 2, the standard defect swatch assembly is seen to comprise rectangular holder 201 which is attached to the instrument frame (not shown) in order to position a standard swatch 202 just outside the edge of web 18 and in the ambit of the laser beam scan. The standard defect swatch comprises a relatively large area (about 7.6 cm. × 17.8 cm.) of acceptable web. Superimposed on this area are two or more areas containing defects which are considered objectionable in density or color. Each such standard defect is chosen with a physical size which would be considered objectionable and should lead to a rejection if found on production web. At least one of the standard defects is an area of lesser density or lighter color (e.g., a hole) whereas at least one other standard defect is a darker than normal area such as a clump of surplus fibers in the case of a web made of nonwoven fibrous materials. Thus at least one standard defect will produce a large positive signal and at least one will provide a large negative signal when scanned by the apparatus. In the interest of simplicity, the preferred embodiment will be described as having only two standard defects, one positive and the other negative, with respect to the type of signal produced.

Returning now to FIG. 1B, the self-check and semi-automatic standardization circuitry 250 is seen to comprise six NAND gates designated 251–256. NAND gates are gate circuits with more than one input which produce a logic low output signal when logic high input signals are supplied simultaneously to all inputs of the gate circuit. NOR gates as described hereinafter are gate circuits with one or more inputs which produce a logic high output when a logic low signal is applied to any one or both of the inputs of the gate circuit. The input of NAND gate 251 is received over line 32a from amplitude comparator 32 and from product gating line 22b from gate generator 222. Similarly, NAND gate 252 receives its inputs from comparator 34 over line 34a and from line 22b. The output terminals of these two NAND gates are connected to the two input terminals of NOR gate 261 whose output passes through inverter 275 and thence to the one-shot multivibrator 271 which serves to actuate driver 281 which in turn lights product noise level indicator lamp 291. Returning to the third and fourth NAND gates, NAND gate 253 receives its inputs from comparator 44 over line 44a and from line 22b, whereas NAND 254 receives its inputs from comparator 46 over line 46a and from line 22b. The outputs of NAND gates 253, 254 are connected to the two input terminals of NOR gate 262, the output of which passes through inverter 276, activates one-shot multivibrator 272 and causes driver 282 to operate product large defect indicator lamp 292. NAND gate 255 receives its input signals from line 44a and from self-check gating circuit output line 22c whereas NAND gate 256 receives its input from 22c and from line 46a. The output of NAND gate 255 activates one-shot multivibrator 273 whose output terminal connects to a first input terminal of NOR gate 263 while the output of NAND gate 256 activates one-shot multivibrator 274 whose output terminal connects to the other input terminal of NOR gate 263. The output of NOR gate 263 is fed to the set terminal of a flip-flop circuit 277 which is employed to turn on (until manually reset) driver 283 for self-check alarm indicator lamp 293. A switch 278 and a high logic level voltage source 279 are used to provide manual reset for the flip-flop 277.

In this preferred embodiment, the NAND and NOR gates are typically Digital Equipment Corporation (DEC) catalog No. M115's. The one-shot multivibrators are DEC M306's with one-shot multivibrators 273, 274 operated in the integrating mode. The flip-flop 277 is a DEC M205, the drivers are DEC M306's and the inverters are DEC M111's.

The gate generator 222 produces output gating signals as a result of the cooperative, conventional functioning of counters, decoders and logic elements (not shown).

In operation, as the scanning beam 16 scans across standard defect swatch 202 and moving product web 18, a double pedestal type signal 59 is produced such as shown in FIG. 3A. The DC extractor circuit 24 then operates on this signal using composite gating signal 60 (FIG. 3B) received over line 22a to provide a signal 61 whose pedestal values have been restored to vary about a zero volt level, shown in FIG. 3C. The positive and negative signal amplitude excursions across the preestablished thresholds established for both standard defect swatch and the product web portions of the scan are detected by comparators 34, and 32, respectively, to produce logic level pulse outputs corresponding to those signals. FIG. 3d shows, for example, the corresponding comparator 32 output pulses 63 for negative going signal excursion across the level set by potentiometer 31. After passing through buffers 36 and 38, the comparator output pulses operate signal switched integraters, 40, 42 to produce ramp shaped pulses 65 such as shown in FIG. 3E which refers only to the output of integrator 40. Those signal amplitudes which exceed secondary threshold values set by potentiometers 45 and 47 result in large defect logic level pulses at the outputs of duration comparators 44 and 46, respectively. FIG. 3F shows, for example negative large defect output signals 67 from comparator 44. Comparator 44 and 46 output signals travel along lines 44a and 46a to be NANDed with self-check gate signal 64 (FIG. 3G) by NAND gates 255, 256 whose outputs operate one-shot multivibrators 273, 274, respectively. FIG. 3H shows the inverted output pulse signal 69 from NAND gate 255. This is normally a recurrent signal and indicates that the inspector system has detected the large high density portion of the standard defect swatch 201. In a like fashion, NAND gate 256 produces a pulse signal each time the large low density or hole condition standard defect is detected.

Triggered by these standard defect pulse signals, one-shot multivibrators 273, 274 produce overlapping long duration high logic level pulses, each of which exceeds the scan repetition interval, thereby maintaining NOR gate 263 output at a low logic level. As long as NOR gate 263 output remains low, the flip-flop 277 does not set and driver 283 cannot illuminate self-check alarm indicator lamp 293. However, should the inspector discriminator circuitry fail to detect either one or the other or both of the defects on the standard swatch 201, or if the gate generator should malfunction, a logic low signal will appear on one or both of NOR gate 263 input terminals and NOR gate 263 output will be a logic high signal. This high logic signal will set the flip-flop 277 and cause the self-check alarm indicator lamp 293 to light. Not until the inspector operator manually resets the flip-flop will the lamp 293 go out and then only if the fault condition has been corrected. FIG. 3I shows one-shot 273 output signal over a series of scans.

For initial system calibration, the operator first observes product noise level lamp 291 (FIG. 1B) and adjusts the potentiometers 31 and 33 (FIG. 1A) until this lamp begins to flash on and off which occurs each time the product noise signal peaks just exceed the adjusted thresholds. Once these amplitude discriminator thresholds have been established, the operator then observes self-check alarm indicator lamp 293 and adjusts potentiometers 45 and 47 until lamp 293 can be extinguished by depressing reset switch 278. This occurs when the threshold values corresponding to both calibration defect durations (sizes) and amplitudes (densities) are set and ready for use as product rating criteria. When both of these steps have been carried out, calibration of the inspector system is complete.

If during subsequent operation of the instrument lamp 293 should come on, it is an indication to the operator that the system should be checked for proper gate generator operations or recalibrated as the lamp turns on only when either the amplitude or duration defect discriminator levels have drifted out of calibration or there has been a deterioration in scanning beam intensity or a fault in the gating has occurred. Thus, the SAS circuitry automatically alerts the operator if proper calibration factors no longer are in effect for his system or that scan beam power is no longer at its proper level.

Thus, there is provided by this invention an improved flying spot web inspection system wherein the improvement enables self-checking of the gate generator as well as the amplitude and duration discriminator sensitivity levels to provide a continuing check of the proper operation of the inspection system.

What is claimed is:

1. In an inspection system for webs that includes means scanning the web for detecting defects in the web and generating output signals representative of said defects, and discriminator circuitry actuated by said output signals for generating alarm signals when said output signals exceed predetermined threshold levels, the improvement comprising: a swatch assembly containing standard defects located adjacent said web in the path of the means for scanning the web, there being output signals normally exceeding said predetermined threshold levels generated during each scan of said swatch assembly; and means for indicating when said inspection system fails to detect said standard defects in each scan.

2. The system as defined in claim 1, said threshold levels being primary threshold levels relating to output signal amplitude discrimination in positive and negative directions and secondary threshold levels relating to signal duration of those output signals exceeding primary threshold levels in positive or negative directions.

* * * * *